US012708631B2

(12) United States Patent
Pappas

(10) Patent No.: US 12,708,631 B2
(45) Date of Patent: Aug. 18, 2026

(54) COMPOSITIONS COMPRISING CANNABINOIDS AND METHODS OF USE THEREOF

(71) Applicant: Schedule 1 Therapeutics, Inc., Oak Park, IL (US)

(72) Inventor: George D. Pappas, Oak Park, IL (US)

(73) Assignee: Schedule 1 Therapeutics, Inc., Chicago, IL (US)

( * ) Notice: Subject to any disclaimer, the term of this patent is extended or adjusted under 35 U.S.C. 154(b) by 908 days.

(21) Appl. No.: 17/429,259

(22) PCT Filed: Feb. 10, 2020

(86) PCT No.: PCT/US2020/017512

§ 371 (c)(1),
(2) Date: Aug. 6, 2021

(87) PCT Pub. No.: WO2020/163866

PCT Pub. Date: Aug. 13, 2020

(65) Prior Publication Data

US 2022/0110887 A1 Apr. 14, 2022

Related U.S. Application Data

(60) Provisional application No. 62/837,577, filed on Apr. 23, 2019, provisional application No. 62/826,562, filed on Mar. 29, 2019, provisional application No. 62/803,185, filed on Feb. 8, 2019.

(51) Int. Cl.

| | |
|---|---|
| ***A61K 31/00*** | (2006.01) |
| ***A61K 45/06*** | (2006.01) |
| ***A61P 25/06*** | (2006.01) |

(52) U.S. Cl.

CPC ............ *A61K 31/658* (2023.05); *A61K 45/06* (2013.01); *A61P 25/06* (2018.01)

(58) Field of Classification Search

CPC ...... A61K 31/05; A61K 45/06; A61K 9/0019; A61K 31/352; A61P 25/06

See application file for complete search history.

(56) References Cited

U.S. PATENT DOCUMENTS

| | | | | |
|---|---|---|---|---|
| 11,607,400 | B2 * | 3/2023 | Pappas | A61P 25/04 |
| 11,712,431 | B2 * | 8/2023 | Pappas | A61K 31/05 514/456 |
| 12,029,721 | B2 * | 7/2024 | Pappas | A61K 45/06 |
| 2017/0348276 | A1 * | 12/2017 | Bryson | A61K 36/577 |
| 2018/0221396 | A1 | 8/2018 | Chadeayne | |
| 2018/0289665 | A1 * | 10/2018 | Turner | A61K 36/185 |
| 2019/0031745 | A1 | 1/2019 | Bigal et al. | |

FOREIGN PATENT DOCUMENTS

| | | | |
|---|---|---|---|
| WO | 2014/159688 | A1 | 10/2014 |
| WO | 2017/185038 | A1 | 10/2017 |
| WO | 2017/218853 | A1 | 12/2017 |
| WO | 2018/106108 | A1 | 6/2018 |
| WO | 2018/152334 | A1 | 8/2018 |
| WO | 2019/056123 | A1 | 3/2019 |
| WO | 2019/145507 | A1 | 8/2019 |

OTHER PUBLICATIONS

Baron, Patterns of medicinal cannabis use, strain analysis, and substitution effect among patients with migraine, headache, arthritis, and chronic pain in a medical cannabis cohort, (The Journal of Headache and Pain, 19:37). (Year: 2018).*

Baron, EP et al., "Patterns of medicinal cannabis use, strain analysis, and substitution effect among patients with migraine, headache, arthritis, and chronic pain in a medicinal cannabis cohort," The Journal of Headache and Pain, May 24, 2018, 19(1):1-28.

Pulling, L, "EAN 2017: Cannabinoids suitable for migraine prophylaxis." Webpage [online], Jun. 26, 2017, retrieved on Apr. 24, 2020, accessed at: https://www.neuro-central.com/ean-2017-cannabinoids-suitable-migraine-prophylaxis/.

International Search Report and Written Opinion for PCT/US2020/17512 dated May 26, 2020, 13 pages.

Extended European Search Report for European Application No. 20753070.0 dated Oct. 10, 2022; 8 pages.

Baron, Eric P. "Medicinal Properties of Cannabinoids, Terpenes, and Flavonoids in Cannabis, and Benefits in Migraine, Headache, and Pain: An Update on Current Evidence and Cannabis Science" Headache, 2018, 58 (7):1139-1186.

Lewis, M. et al. "Chemical Profiling of Medical Cannabis Extracts", ACS Omega, 2017, 2(9):6091-6103.

* cited by examiner

*Primary Examiner* — Kamal A Saeed
*Assistant Examiner* — Meghan C Heasley
(74) *Attorney, Agent, or Firm* — POLSINELLI PC

(57) ABSTRACT

The present disclosure is related to the use of compositions and their use in reducing pain.

8 Claims, No Drawings

COMPOSITIONS COMPRISING CANNABINOIDS AND METHODS OF USE THEREOF

CROSS REFERENCE TO RELATED APPLICATIONS

This application claims the benefit of International Application No. PCT/US2020/017512, filed Feb. 10, 2020, which claims the benefit of U.S. Provisional Patent Application Ser. No. 62/803,185 filed Feb. 8, 2019, U.S. Provisional Patent Application Ser. No. 62/826,562, filed Mar. 29, 2019, and U.S. Provisional Patent Application Ser. No. 62/837,577, filed Apr. 23, 2019, each of which is hereby incorporated by reference.

FIELD OF THE DISCLOSURE

The present disclosure is related to the use of compositions comprising cannabinoids and their use in reducing pain.

BACKGROUND OF THE DISCLOSURE

In the U.S., more than 38 million people suffer from migraines. This translates into roughly 13 percent of adults in the U.S. population, or slightly more than one in ten people. Of those, 2-3 million migraine suffers are considered chronic.

Fibromyalgia is a common chronic pain disorder. It affects an estimated 10 million people in the U.S. and an estimated 3-6% of the world population. While it is most prevalent in women (75-90 percent of those diagnosed with fibromyalgia are women), it also occurs in men and children of all ethnic groups.

Treatment of migraine pain, frequency, and fibromyalgia pain includes the use of FDA-approved therapies, and non-FDA approved alternative treatments, such as cannabinoids. For instance, current treatments may include the triptan class of drugs, which exert their effect via 5HT-1B/1D receptor agonism, ergotamines, NSAIDs, opioids, simple analgesics, barbiturates, anti-epileptic drugs, tricyclic anti-depressants, COX-2 inhibitors, CGRP inhibitors, beta and calcium channel blockers, anti-hypertensives, antihistamines, onabotulinumtoxinA (Botox®) and others.

Such treatments, however, often fail to help those diagnosed with either disorder. Hence, there is a need in the art for an effective treatment of pain associated with an attack of migraine with and/or without aura, migraine frequency, or fibromyalgia pain as well as related disorders such as familial hemiplegic migraine, sporadic hemiplegic migraine, and complex regional pain syndrome.

DETAILED DESCRIPTION

The present disclosure details compositions comprising at least one cannabinoid. For instance, in some embodiments, the present disclosure details methods of using compositions comprising at least one minor cannabinoid for pain associated with an attack of migraine with and/or without aura, migraine frequency, and fibromyalgia pain as well as related disorders such as familial hemiplegic migraine, sporadic hem iplegic migraine, and complex regional pain syndrome. In addition, such compositions may be used to alleviate other symptoms associated with migraine, such as photophobia, phonophobia, and nausea.

In additional aspects, the present disclosure details compositions comprising THC and CBD. Specifically, a composition of the disclosure may comprise THC and an amount of CBD to reduce any unwanted side effects of THC or risk factors associated with THC, or to increase efficacy of THC or of the composition. Non-limiting examples of side effects or risk factors include psychoactivity, psychosis, anxiety, paranoia, dizziness, confusion, cardiovascular risk, memory impairment, or combinations thereof. Additionally, the present disclosure details methods of using such compositions for pain associated with an attack of migraine with and/or without aura, migraine frequency, and fibromyalgia pain as well as related disorders such as familial hem iplegic migraine, sporadic hem iplegic migraine, and complex regional pain syndrome.

I. Minor Cannabinoid Compositions

A minor cannabinoid composition of the present disclosure comprises at least one minor cannabinoid. In some embodiments, a composition may further comprise a major cannabinoid, a terpenoid, an additional compound, or a combination thereof.

A minor cannabinoid composition of the present disclosure, when administered to a subject in need thereof, modulates biomarkers of central and peripheral sensitization. As used herein, the phrase peripheral sensitization refers to hypersensitivity in peripheral nociceptors which cause phenomena such as reduced stimulus threshold (allodynia), increase in response and prolonged after effects (hyperalgesia), and expansion of the receptive field to non-injured tissue, and hypersensitivity of peripheral ocular and auditory neural pathways which cause phenomena such as photophobia and phonophobia. As used herein, "central sensitization" refers to the hyperexcitable activity of central nociceptive neural pathways and central ocular and auditory pathways which cause phenomena such as photophobia and phonophobia.

A minor cannabinoid composition of the present disclosure may modulate biomarkers of central and peripheral sensitization by binding as an agonist, antagonist, or inverse agonist to one or more receptors from the group consisting of CB1, CB2 (in the dorsal horn, spinal cord), TRPV-1, TRPV-2, TRPV-3, TRPV-4, TRPV-8, TRPA-1, TRPM-8, 5HT-1A, 5HT-2A, Type 3 5HT, alpha-2 adrenoceptor, PPAR-gamma, GAPDH, PPAR, GPCR-92 NK1, EP, trkB, mGlu1, mGlu4, mGlu5 mGlu6, mGlu7, mGlu8, FAAH, NMDA and its subunits NR1 and NR2A.

In some embodiments, a minor cannabinoid composition of the present disclosure may modulate 5-HT receptors (including 5HT-1B/1D receptors), suppress glutamatergic release via CB1 receptor mediated inhibition of NMDA, activate TRPV receptors to modulate CGRP release and influence vasomotor tone, increase AEA levels in cerebrospinal fluid and in the PAG, or decrease CGRP and NO. In preferred embodiments, a minor cannabinoid composition of the present disclosure may modulate biomarkers of central and peripheral sensitization by binding as an agonist, antagonist, or inverse agonist to one or more receptors from the group consisting of CB1, CB2, TRPV1, TRPV2, NMDA and glutamate receptors.

Biomarkers of central and peripheral sensitization may include NMDA, CGRP, FAAH, Substance P, Glutamate, NO, GABA, NGF, serotonin, dopamine, AEA, 2-AG, and others. In some embodiments, biomarkers of peripheral sensitization may include neurogenic CGRP, nitric oxide, or other compounds to inhibit dural blood vessel dilation.

In certain embodiments, a minor cannabinoid composition of the invention may decrease the activity of enzymes that act as biomarkers, such as cyclooxygenase, lipoxygenase and P450-type enzymes such as CYP1A1, CYP1A2, CYP2B6, CYP2C9, CYP3A4, CYP3A5, CYP2A6, CYP2D6, CYP1B1, and/or CYP3A7. Decreasing the activity of one or more of these enzymes may modulate the anti-inflammatory effects that are implicated in migraine pain.

In particular embodiments, a minor cannabinoid composition of the invention may exhibit other forms of anti-nociception by inhibiting NF-kB activity, iNOS, corticotropin releasing factor binding protein, cysteine protease ATGB4, photoreceptor-specific nuclear receptor NR2E3, or diacylglycerol lipase. In additional particular embodiments, a minor cannabinoid composition of the invention may modulate levels of NMDA, alpha amino-3-hydroxyl-5-methyl-4-isoxazole-proprionate, and kainate receptor modulated neuro-toxicities via CB1, or suppress glutamatergic release by inhibiting modulation of NMDA, mediated by CB1, or increase endo-opioid pre-curser gene expression involved in pain perception. In preferred embodiments, a composition of the present disclosure may affect sensitization by modulating levels of NMDA and/or glutamate.

(a) Minor Cannabinoids

A minor cannabinoid composition of the present disclosure comprises at least one minor cannabinoid. Minor cannabinoids used in the present disclosure may be isolated from natural sources or synthetically manufactured. Non-limiting examples of minor cannabinoids may include CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In one embodiment, a minor cannabinoid composition of the present disclosure may comprise one or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In another embodiment, a minor cannabinoid composition of the present disclosure may comprise two or more, three or more, four or more, five or more, six or more, seven or more, eight or more, nine or more, or ten or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In yet another embodiment, a minor cannabinoid composition of the present disclosure may comprise at least 11, at least 12, at least 13, at least 14, at least 15, at least 16, at least 17, at least 18, at least 19, at least 20, at least 21 or at least 22 or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol.

In some embodiments, the at least one minor cannabinoid is selected from the group consisting of CBG, CBGA, CBN, CBNA, THCV, THCA, CBC, CBCA, CBDV, or D8-THC. In certain embodiments, a minor cannabinoid composition of the present invention comprises at least two, three, four, five, six, seven, eight, nine or ten minor cannabinoid(s) selected from the group consisting of CBG, CBGA, CBN, CBNA, THCV, THCA, CBC, CBCA, CBDV, or D8-THC. In particular embodiments, a minor cannabinoid composition of the invention may comprise any combination of CBG, CBGA, CBN, CBNA, THCV, THCA, CBC, CBCA, CBDV, or D8-THC.

A minor cannabinoid composition of the disclosure may comprise from about 1% to about 100% of one or more minor cannabinoids. For instance, a minor cannabinoid composition may comprise about 5, 10, 15, 20, 25, 30, 35, 40, 45, 50, 55, 60, 65, 70, 75, 80, 85, 90, or 95% of one or more minor cannabinoids. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 100% of one or more minor cannabinoids.

(b) Major Cannabinoids

A minor cannabinoid composition of the present disclosure may comprise a major cannabinoid. Non-limiting examples of a major cannabinoid may include cannabinoid D-9THC (THC) and CBD. In one embodiment, a minor cannabinoid composition of the present disclosure comprises THC. In another embodiment, a minor cannabinoid composition of the present disclosure comprises CBD. In a preferred embodiment, a minor cannabinoid composition of the invention may comprise both THC and CBD.

A minor cannabinoid composition of the disclosure may comprise from about 1% to about 99% of one or more major cannabinoids. For instance, a composition may comprise about 5, 10, 15, 20, 25, 30, 35, 40, 45, 50, 55, 60, 65, 70, 75, 80, 85, 90, or 95% of one or more major cannabinoids. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of one or more major cannabinoids.

(c) Terpenoids

In certain embodiments, a minor cannabinoid composition of the invention may comprise a terpenoid. Non-limiting examples of terpenoids may include myrcene, β-caryophyllene, limonene, α-terpineol, linalool, α-phellandrene, α-pinene, β-pinene, γ-terpinene, nerolidol, phytol, caryophyllene oxide and α-humule. In some embodiments, a minor cannabinoid composition of the present disclosure may comprise one, two, three, four, five, or more than five terpenoids selected from the group consisting of myrcene, β-caryophyllene, limonene, α-terpineol, linalool, α-phellandrene, α-pinene, β-pinene, γ-terpinene, nerolidol, phytol, caryophyllene oxide and α-humule.

Generally speaking the at least one terpenoid may comprise from 0% to about 99% of a composition of the present disclosure by weight. For instance, a minor cannabinoid composition may comprise about 5, 10, 15, 20, 25, 30, 35, 40, 45, 50, 55, 60, 65, 70, 75, 80, 85, 90, or 95% of at least one terpenoid by weight. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of at least one terpenoid by weight.

(d) Other Compounds

In certain embodiments, a minor cannabinoid composition of the invention may comprise one or more additional compounds. Non-limiting examples of additional compounds may include a simple analgesic like paracetamol and/or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound. In some embodiments, a minor cannabinoid composition of the present disclosure may comprise one, two, three, four, five, or more than five additional compounds selected from the group consisting of a simple analgesic like paracetamol or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound.

Generally speaking the at least one additional compound may comprise from 0% to about 99% of a minor cannabinoid composition of the present disclosure by weight. For instance, a minor cannabinoid composition may comprise about 5, 10, 15, 20, 25, 30, 35, 40, 45, 50, 55, 60, 65, 70, 75, 80, 85, 90, or 95% of one or more additional compounds. In some embodiments, a minor cannabinoid composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of one or more additional compounds.

(e) Amounts

Generally speaking, a minor cannabinoid composition of the present disclosure may be used to deliver about 20, 30, 40, 50, 60, 70, 80, 90, 100, 110, 120, 130, 140, 150, 160, 170, 180, or more than 180 mg/day of THC. In certain embodiments, up to 40 mg THC is delivered per day. In other embodiments, up to about 120 mg THC is delivered per day. These amounts may be comprised in a single dose, or more than one dose (e.g. two, three, or more than three doses).

A minor cannabinoid composition of the present disclosure may be used to deliver about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD. These amounts may be comprised in a single dose, or more than one dose (e.g. two, three, or more than three doses). In particular embodiments, a greater amount of CBD is included in a minor cannabinoid composition to treat the inflammation component in migraine, to counteract psychoactivity or undesired side effects of THC or the minor cannabinoids, or a combination thereof.

In certain embodiments, a minor cannabinoid composition of the present disclosure may be used to deliver about 20, 30, 40, 50, 60, 70, 80, 90, 100, 110, 120, 130, 140, 150, 160, 170, 180, or more than 180 mg/day of THC and about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD. These amounts may be comprised in a single dose, or more than one dose (e.g. two, three, or more than three doses).

In some embodiments, a minor cannabinoid composition of the present disclosure may be used to deliver about 20, 30, 40, 50, 60, 70, 80, 90, 100, 110, 120, 130, 140, 150, 160, 170, 180, or more than 180 mg/day of a minor cannabinoid. These amounts may be comprised in a single dose, or more than one dose (e.g. two, three, or more than three doses). In each of the embodiments where a composition of the present disclosure comprises a minor cannabinoid, the composition may further by used to deliver about 20, 30, 40, 50, 60, 70, 80, 90, 100, 110, 120, 130, 140, 150, 160, 170, 180, or more than 180 mg/day of THC, or about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD, or a combination thereof.

II. THC and CBD Compositions

A THC and CBD composition of the present disclosure comprises THC and CBD. Specifically, a THC and CBD composition of the disclosure comprises THC and an amount of CBD to reduce any unwanted side effects of THC or risk factors associated with THC, or increase efficacy of THC or of the composition. Non-limiting examples of side effects or risk factors include psychoactivity, psychosis, anxiety, paranoia, dizziness, confusion, cardiovascular risk, memory impairment, or combinations thereof. In some embodiments, a THC and CBD composition may further comprise at least one minor cannabinoid, a terpenoid, an additional compound, or a combination thereof.

A THC and CBD composition of the present disclosure, when administered to a subject in need thereof, modulates biomarkers and behavioral indicators of central and peripheral sensitization. As used herein, the phrase peripheral sensitization refers to hypersensitivity in peripheral nociceptors which cause phenomena such as reduced stimulus threshold (allodynia), increase in response and prolonged after effects (hyperalgesia), and expansion of the receptive field to non-injured tissue. As used herein, "central sensitization" refers to the hyperexcitable activity of central nociceptive neural pathways.

A THC and CBD composition of the present disclosure may modulate biomarkers of central and peripheral sensitization by binding as an agonist, antagonist, or inverse agonist to one or more receptors from the group consisting of CB1, CB2 (in the dorsal horn, spinal cord), TRPV-1, TRPV-2, TRPV-3, TRPV-4, TRPV-8, TRPA-1, TRPM-8, 5HT-1A, 5HT-2A, Type 3 5HT, alpha-2 adrenoceptor, PPAR-gamma, GAPDH, PPAR, GPCR-92 NK1, EP, trkB, mGlu1, mGlu4, mGlu5 mGlu6, mGlu7, mGlu8, FAAH, NMDA and its subunits NR1 and NR2A.

In some embodiments, a THC and CBD composition of the present disclosure may indirectly modulate 5-HT receptors (including 5HT-1B/1D receptors), suppress glutamatergic release via CB1 receptor mediated inhibition of NMDA, activate TRPV receptors to modulate CGRP release and influence vasomotor tone, increase AEA levels in cerebrospinal fluid and in the PAG, or decrease CGRP and NO. In preferred embodiments, a composition of the present disclosure may modulate biomarkers of central and peripheral sensitization by binding as an agonist, antagonist, or inverse agonist to one or more receptors from the group consisting of CB1, CB2, TRPV1, TRPV2, NMDA and glutamate receptors.

Biomarkers of central and peripheral sensitization may include NMDA, CGRP, FAAH, Substance P, Glutamate, NO, GABA, NGF, serotonin, dopamine, NO, AEA, 2-AG, and others. In some embodiments, biomarkers of peripheral sensitization may include neurogenic CGRP, nitric oxide, or other compounds to inhibit dural blood vessel dilation.

In certain embodiments, a THC and CBD composition of the invention may decrease the activity of enzymes that act as biomarkers, such as cyclooxygenase, lipoxygenase and P450-type enzymes such as CYP1A1, CYP1A2, CYP2B6, CYP2C9, CYP3A4, CYP3A5, CYP2A6, CYP2D6, CYP1B1, and/or CYP3A7. Decreasing the activity of one or more of these enzymes may modulate the anti-inflammatory effects that are implicated in migraine pain.

In particular embodiments, a THC and CBD composition of the invention may exhibit other forms of anti-nociception by inhibiting NF-kB activity, iNOS, corticotropin releasing factor binding protein, cysteine protease ATGB4, photoreceptor-specific nuclear receptor NR2E3, or diacylglycerol lipase. In additional particular embodiments, a THC and CBD composition of the invention may modulate levels of NMDA, alpha amino-3-hydroxyl-5-methyl-4-isoxazole-proprionate, and kainate receptor modulated neuro-toxicities via CB1, or suppress glutamatergic release by inhibiting modulation of NMDA, mediated by CB1, or increase endo-opioid pre-curser gene expression involved in pain perception. In preferred embodiments, a THC and CBD composition of the present disclosure may affect sensitization by modulating levels of NMDA and/or glutamate.

Behavioral indicators may include behavioral responses in animal or human models of trigeminovascular nociception, animal models of spontaneous nociceptive responses in the craniofacial region or plantar region, models of associated neurological symptoms, models of associated symptoms of migraine or sensitization such as photophobia, phonophobia, osmophobia, allodynia, or other symptoms, or other animal or human models.

(a) THC and CBD

A THC and CBD composition of the present disclosure comprises THC (cannabinoid D-9THC) and CBD. Specifically, a composition of the disclosure comprises THC and an amount of CBD to reduce any unwanted side effects of THC or risk factors associated with THC, or increase efficacy of THC. Non-limiting examples of side effects or risk factors include psychoactivity, psychosis, anxiety, paranoia, dizziness, confusion, increased cardiovascular risk, memory impairment, or combinations thereof.

As used herein, THC refers to tetrahydrocannabinol, whether synthetically produced or isolated from a plant. THC may refer to (−)-trans-$\Delta^9$-tetrahydrocannabinol or isomers thereof. As used herein, CBD refers to cannabidiol or isomers thereof, whether synthetically produced or isolated from a plant.

For instance, a THC and CBD composition of the present disclosure may comprise from about 0.1% to about 99% of THC. For instance, a THC and CBD composition may comprise about 5, 10, 15, 20, 25, 30, 35, 40, 45, 50, 55, 60, 65, 70, 75, 80, 85, 90, or 95% of THC. In some embodiments, a THC and CBD composition may comprise about 0.1 to about 0.5, about 0.5 to about 1, about 1 to about 2, about 2 to about 5, about 5 to about 10, about 5 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of THC.

In each of the above embodiments, a THC and CBD composition of the disclosure further comprises CBD. For instance, a THC and CBD composition of the disclosure may comprise from about 1% to about 99.9% of CBD. For instance, a composition may comprise about 5, 10, 15, 20, 25, 30, 35, 40, 45, 50, 55, 60, 65, 70, 75, 80, 85, 90, 95, 98, 98.5, 99, 99.5, 99.7, or 99.9% of CBD. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, about 80 to about 95, about 95 to about 98, about 98 to about 99.9% of CBD.

In certain embodiments, a THC and CBD composition of the present disclosure comprises about 80% CBD to about 99.9% CBD, and about 0.1% THC to about 20% THC. In particular embodiments, a THC and CBD composition of the present disclosure comprises about 90% CBD to about 97% CBD and about 3% THC to about 10% THC. In preferred embodiments, a THC and CBD composition may comprise at least about 90% CBD and no more than about 10% THC. For instance, a THC and CBD composition may comprise at least about 90, 91, 92, 93, 94, 95, 96, 97, or 98% CBD and no more than about 10, 9, 8, 7, 6, 5, 4, 3, or 2% THC. In other preferred embodiments, a THC and CBD composition may comprise at least about 95% CBD and no more than about 5% THC. For instance, a THC and CBD composition may comprise at least about 95, 96, 97, 98.5, 99, 99.5, or 99.9% CBD and no more than about 5, 4, 3, 2, 1.5, 1, 0.5, or 0.1% THC.

CBD in a composition of the disclosure may reduce the psychoactive side effects or risk factors of THC or other cannabinoids as measured by levels of prolactin, c-Fox expression, anandamide (AEA) in serum and/or cerebral spinal fluid (CSF), GABA, glutamate, FAAH, ethanolamide (palmitoylethanolamide and oleoylethanolamide), FLAT (FAAH-like anandamide transporter), or other fatty acid binding proteins (FABPs).

CBD may exert its antipsychotic effects as measured by acting as an antagonist, agonist, or inverse agonist to receptors CB1, CB2, and TRPV1 in the prefrontal cortex, amygdala and/or hippocampus, GABAergic neurons in the nucleus accumbens, 5HT-1A, D2, PPARγ (peroxisome proliferator activated receptor gamma), or by interacting with ion channels or enzymes, as described herein, contributing to its anti-inflammatory, anti-oxidative, and/or neuroprotective properties.

CBD's anti-psychotic effects may be measured in the striatum and temporal cortex, ventral tegmental area (VTA), nucleus accumbens, ventral pallidum, mediodorsal thalamic nucleus, prefrontal cortex, anterior cingulate, parahippocampal gyrus, amygdala, right posterior temporal gyrus and right temporal lobe, middle occipital gyrus, cerebellum, left caudate, or dopaminergic mesolimbic pathway.

CBD's anti-psychotic effects may be measured by reduction of psychotomimetic symptoms, amorphine-induced stereotyped behavior, amphetamine, D-amphetamine, and ketamine induced hyperlocomotion, social withdrawal in animal models, reduced scores of Brief Psychiatric Rating Scale (BPRS), Parkinson Psychosis Questionnaire, Positive and Negative Syndrome Scale (PANSS), various other behavioral and neurochemical techniques in animal models, such as apomorphine stereotypy, catalepsy, MK-801 Prepulse inhibition (PPI), hyperlocomotion, or social withdrawal, c-Fos immunohistochemistry, or other techniques.

Methods of isolating, synthesizing, or purifying THC and CBD are known in the art.

(b) Minor Cannabinoids

A THC and CBD composition of the present disclosure may further comprise at least one minor cannabinoid. Minor cannabinoids used in the present disclosure may be isolated from natural sources or synthetically manufactured. Non-limiting examples of minor cannabinoids may include CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In one embodiment, a THC and CBD composition of the present disclosure may comprise one or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In another embodiment, a THC and CBD composition of the present disclosure may comprise two or more, three or more, four or more, five or more, six or more, seven or more, eight or more, nine or more, or ten or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol. In yet another embodiment, a THC and CBD composition of the present disclosure may comprise at least 11, at least 12, at least 13, at least 14, at least 15, at least 16, at least 17, at least 18, at least 19, at least 20, at least 21 or at least 22 or more of the group of minor cannabinoids consisting of CBGV (cannabigerovarin), CBGVA (cannabigerovarinic acid), CBG (cannabigerol), CBGA (cannbigerolic acid), Cannabinerolic acid, Cannabinerol, CBN (cannabinol), CBNA (cannabinolic acid), THCV (tetrahydrocannabivarin), THCA (tetrahydrocannabinolic acid), D8-THC (delta-8-tetrahydrocannabinol), CBDA (cannabidiolic acid), CBC (cannabichromene), CBCA, (cannabichromenic acid), CBDV (cannabivarin), CBL (Cannabicyclol), CBLA (Cannabicyclolic acid), Cannabicyclovarin, CBE (cannabielsoin), CBF (cannabifuran), Cannabicitran, Cannabitriol, and Cannabiorcol.

In some embodiments, a minor cannabinoid may be selected from the group consisting of CBG, CBGA, CBN, CBNA, THCV, THCA, CBC, CBCA, CBDV, or D8-THC. In certain embodiments, a THC and CBD composition of the present invention may comprise at least two, three, four, five, six, seven, eight, nine or ten minor cannabinoid(s) selected from the group consisting of CBG, CBGA, CBN, CBNA, THCV, THCA, CBC, CBCA, CBDV, or D8-THC. In particular embodiments, a THC and CBD composition of the invention may comprise any combination of CBG, CBGA, CBN, CBNA, THCV, THCA, CBC, CBCA, CBDV, or D8-THC.

A THC and CBD composition of the disclosure may comprise from about 1% to about 99.9% of one or more minor cannabinoids. For instance, a THC and CBD composition may comprise about 0.1, 0.5, 1.5, 2, 2.5, 3, 4, 5, 10, 15, 20, 25, 30, 35, 40, 45, 50, 55, 60, 65, 70, 75, 80, 85, 90, 95, 96, 97, 98, 99, 99.5, 99.7, 99.9% of one or more minor cannabinoids. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 99% of one or more minor cannabinoids.

In some embodiments, a THC and CBD composition may comprise a ratio of minor cannabinoid to THC of about 5:1, 8:1, 10:1, 12:1, 15:1, 18:1, 20:1, 22:1, 25:1, 28:1, 30:1, 32:1, 35:1, 38:1, 40:1, 50:1, 75:1, 90:1, 100:1, 110:1, 125:1, 150:1, 200:1, 250:1, 400:1, or 500:1. In other embodiments, a THC and CBD composition may comprise a ratio of minor cannabinoid to D8-THC of about 5:1, 8:1, 10:1, 12:1, 15:1, 18:1, 20:1, 22:1, 25:1, 28:1, 30:1, 32:1, 35:1, 38:1, 40:1, 50:1, 75:1, 90:1, 100:1, 110:1, 125:1, 150:1, 200:1, 250:1, 400:1, or 500:1. In still other embodiments a THC and CBD composition may comprise a ratio of minor cannabinoid to THCV of about 5:1, 8:1, 10:1, 12:1, 15:1, 18:1, 20:1, 22:1, 25:1, 28:1, 30:1, 32:1, 35:1, 38:1, 40:1, 50:1, 75:1, 90:1, 100:1, 110:1, 125:1, 150:1, 200:1, 250:1, 400:1, or 500:1. In preferred embodiments, a THC and CBD composition may comprise a ratio of CBC, CBL, CBN, CBG, CBDV, CBC to THC, D8-THC, or THCV of about 5:1, 8:1, 10:1, 12:1, 15:1, 18:1, 20:1, 22:1, 25:1, 28:1, 30:1, 32:1, 35:1, 38:1, 40:1 50:1, 75:1, 90:1, 100:1, 110:1, 125:1, 150:1, 200:1, 250:1, 400:1, or 500:1.

In particular embodiments, a THC and CBD composition may comprise a ratio of D8-THC to D9-THC of about 1:1, 2:1, 3:1, 4:1, 5:1, 6:1, 7:1, 8:1, 9:1, or 10:1. In other embodiments, a THC and CBD composition may comprise a ratio of THCV to D9-THC of about 1:1, 2:1, 3:1, 4:1, 5:1 6:1, 7:1, 8:1, 9:1, or 10:1.

(c) Terpenoids

In certain embodiments, a THC and CBD composition of the invention may comprise a terpenoid. Non-limiting examples of terpenoids may include myrcene, β-caryophyllene, limonene, α-terpineol, linalool, α-phellandrene, α-pinene, β-pinene, γ-terpinene, nerolidol, phytol, caryophyllene oxide and α-humule. In some embodiments, a THC and CBD composition of the present disclosure may comprise one, two, three, four, five, or more than five terpenoids selected from the group consisting of myrcene, β-caryophyllene, limonene, α-terpineol, linalool, α-phellandrene, α-pinene, β-pinene, γ-terpinene, nerolidol, phytol, caryophyllene oxide and α-humule.

Generally speaking the at least one terpenoid may comprise from 0% to about 99.9% of a THC and CBD composition of the present disclosure by weight. For instance, a THC and CBD composition may comprise about 5, 10, 15, 20, 25, 30, 35, 40, 45, 50, 55, 60, 65, 70, 75, 80, 85, 90, 95, 97, 98, 99, 99.5, or 99,% of at least one terpenoid by weight. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, about 60 to about 80, about 65 to about 85, about 70 to about 90, about 75 to about 95, or about 80 to about 90, about 90 to 95, about 95 to 99.9% of at least one terpenoid by weight.

(d) Other Compounds

In certain embodiments, a THC and CBD composition of the invention may comprise one or more additional compounds. Non-limiting examples of additional compounds may include a simple analgesic like paracetamol and/or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound. In some embodiments, a THC and CBD composition of the present disclosure may comprise one, two, three, four, five, or more than five additional compounds selected from the group consisting of a simple analgesic like paracetamol or acetaminophen, a non-steroidal anti-inflammatory drug (NSAID), a 5-HT (serotonin) receptor agonist, a calcitonin gene related peptide (CGRP) receptor antagonist, an N-methyl D-asparate (NMDA) inhibitor, a glutamate receptor antagonist, a Substance P inhibitor, a GABA inhibitor, FAAH inhibitor, a Nerve Growth Factor (NGF) inhibitor, a Brain-Derived Neurotrophic Factor (BDNF) inhibitor, an extracellular signal-regulated kinase (ERK) antagonist, a NO inhibitor, or another compound.

Generally speaking the at least one additional compound may comprise from 0% to about 99% of a THC and CBD composition of the present disclosure by weight. For instance, a composition may comprise about 5, 10, 15, 20, 25, 30, 35, 40, 45, 50, 55, 60, 65, 70, 75, or 80% of one or more additional compounds. In some embodiments, a THC and CBD composition may comprise about 1 to about 25, about 15 to about 35, about 20 to about 40, about 25 to about 45, about 30 to about 50, about 35 to about 55, about 40 to about 60, about 45 to about 65, about 50 to about 70, about 55 to about 75, or about 60 to about 80, about 65 to about 85, about 70 to about 90, about 75 to about 95, or about 80 to about 99% of one or more additional compounds.

(e) Amounts

Generally speaking, a THC and CBD composition of the present disclosure may be used to deliver about 20, 30, 40, 50, 60, 70, 80, 90, 100, 110, 120, 130, 140, 150, 160, 170, 180, or more than 180 mg/day of THC. These amounts may be comprised in a single dose, or more than one dose (e.g. two, three, or more than three doses).

In each of the above embodiments, a THC and CBD composition of the present disclosure may further be used to deliver about 100, 200, 300, 400, 500, 600, 700, 800, 900, 1000, 1100, 1200, 1300, 1400, 1500, 1600, 1700, 1800, 1900, 2000, 2100, 2200, 2300, or 2400 mg/day of CBD. These amounts may be comprised in a single dose, or more than one dose (e.g. two, three, or more than three doses). In particular embodiments, a greater amount of CBD is included in the composition to reduce undesired side effects of THC or risk factors associated with THC, or increase efficacy of THC. Non-limiting examples of side effects or risk factors include psychoactivity, psychosis, anxiety, paranoia, dizziness, confusion, cardiovascular risk, memory impairment, or combinations thereof.

III. Pharmaceutical Compositions

The present disclosure also provides pharmaceutical compositions. A pharmaceutical composition comprises a minor cannabinoid composition (as detailed in section I above) or a THC and CBD composition (as detailed in section II above) and at least one pharmaceutically acceptable excipient. A pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional compounds. Thus, in addition to the therapies described herein, one may also provide to the subject other therapies known to be efficacious for treatment of the disease, disorder, or condition or to reduce side effects. In some embodiments, the additional drug or therapeutically active agent induces anti-inflammatory effects.

(i) Diluent

In one embodiment, the excipient may be a diluent. The diluent may be compressible (i.e., plastically deformable) or abrasively brittle. Non-limiting examples of suitable compressible diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders may include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, C12-C18 fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents may include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives may include antioxidants, such as BHA, BHT, vitamin A, vitamin C, vitamin E, or retinyl palm itate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials may include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A.R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A.R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

IV. Administration (a) Dosage Forms

A composition of the present disclosure may be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration may include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In particular embodiments, the composition may be formulated for sublingual delivery. Sublingual delivery forms (films, tablets, or sprays) are designed to dissolve very rapidly. Examples of such formulations may include ergotamine tartrate, isosorbide dinitrate, isoproterenol HCl, or a combination thereof. The necessary ingredients for the pharmaceutical dosage unit may be processed in accordance with known methods, using or incorporating familiar coatings and additives as required. By way of example only, in addition to the pharmaceutically active components, a dosage unit may contain effective amounts of binders, fillers, disintegrants, sustained-release agents, diluents, anti-adherents, glidants, flow aids, plasticizers and lubricants, which are well known in the field of pharmaceutical processing for sublingual delivery. For instance, the formulation of these tablets may contain, in addition to the active agents, a limited number of soluble excipients, including a binder such as povidone or hydroxypropyl methylcellulose (HPMC), diluents such as lactose, mannitol, starch or cellulose, a disintegrant such as pregelatinized or modified starch, lubricants such as magnesium stearate, stearic acid or hydrogenated vegetable oil, a sweetener such as saccharin or sucrose and suitable flavoring and coloring agents. The process of making sublingual dosage forms may involve, for instance, moistening the blended powder components with an alcohol-water solvent system containing approximately 60% alcohol and 40% water and pressing this mixture into tablets.

In certain embodiments, a composition of the present disclosure may be encapsulated in a suitable vehicle to either aid in the delivery of the compound(s) to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a composition of the present disclosure may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palm itate), n-octadecanoate (stearate), n-eicosanoate (arachidate), n-docosanoate (behenate), n-tetracosanoate (lignocerate), cis-9-hexadecenoate (palm itoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palm itoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of active ingredient (e.g. minor cannabinoid, major cannabinoid, terpenoid, combination thereof, etc.), concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions.

In yet another embodiment, a composition of the present disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

Generally, a safe and effective amount of a composition of the present disclosure is an amount that would cause the desired therapeutic effect in a subject while minimizing undesired side effects. In various embodiments, an effective amount of a composition of the present disclosure may reduce pain associated with an attack of migraine with and/or without aura, may reduce migraine frequency, may reduce fibromyalgia pain, or pain associated with related disorders such as familial hemiplegic migraine, sporadic hem iplegic migraine, and complex regional pain syndrome.

The amount of a composition described herein that can be combined with a pharmaceutically acceptable carrier to produce a single dosage form will vary depending upon the subject treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a composition of the present disclosure can occur as a single event or over a time course of treatment. For example, a composition of the present disclosure may be administered daily, weekly, bi-weekly, or monthly. For treatment of acute conditions, the time course of treatment may be from at least one day to at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities.

(b) Purity

Generally speaking, a compound included in a composition of the disclosure, such as a minor cannabinoid or a major cannabinoid should be of high purity and consistent quality, regardless of source. For instance, a minor or major cannabinoid used in a composition of the disclosure is at least 90, 91, 92, 93, 94, 95, 96, 97, 98 or 99% pure. In certain embodiments, a minor or major cannabinoid used in a composition of the disclosure is at least 95, 96, 97, 98, or 99% pure. In preferred embodiments, a minor or major cannabinoid used in a composition of the disclosure is at least 97% pure.

Manufacture of a compound for a composition of the disclosure is preferred to meet GLP requirements. In certain embodiments, manufacture of a compound for a composition of the disclosure meets GMP requirements to ensure consistent quality.

Quantitative/qualitative methods to confirm quality and purity include use of High Performance Liquid Chromatography (HPLC), Ultra Performance Liquid Chromatography (UPLC), Nuclear Magnetic Resonance (NMR) spectroscopy, Gas Chromatography (GC), Thin Layer Chromatography (TLC), and standard methods for testing for contamination of microbiological, heavy metal, pesticide, or other contaminants.

Generally speaking a composition of the present disclosure has at least 5%, 10%, 15%, 20%, 25%, 30%, 40%, 50%, 60%, 70%, 80%, 90%, or 95% fewer side effects than if the minor and major cannabinoids are not at least 90% pure. Side effects, as used herein, refer to any effects of the present composition other than reducing pain, photophobia, phonophobia, or nausea associated with an attack of migraine with and/or without aura, migraine frequency, and fibromyalgia pain as well as related disorders such as familial hemiplegic migraine, sporadic hemiplegic migraine, and complex regional pain syndrome.

V. Methods

Another aspect of the present disclosure is methods of using the compositions described in the above sections.

(a) Methods of Reducing Migraine Pain with a Minor Cannabinoid Composition

A minor cannabinoid composition of the present disclosure may be used in a method of reducing migraine pain. Generally speaking, such a method would comprise administering a pharmaceutically effective amount of at least one minor cannabinoid alone, or in combination with THC, CBD, or both, such that at least one biomarker of central and peripheral sensitization is modulated and migraine pain is reduced in the subject.

In some embodiments, the at least one minor cannabinoid, detailed in section I above, may be a phytocannabinoid. As used herein, the term "phytocannabinoid" refers to a cannabinoid isolated from a non-synthetic source.

In certain embodiments, the migraine pain is acute migraine pain. Generally speaking, a method of the invention is used for a subject suffering from an acute migraine. Methods of diagnosing acute migraine are known in the art.

In some embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

(b) Methods of Reducing Migraine Pain with a THC and CBD Composition

A THC and CBD composition of the present disclosure may be used in a method of reducing migraine pain while reducing unwanted side effects of THC or risk factors associated with THC. Non-limiting examples of side effects or risk factors include psychoactivity, psychosis, anxiety, paranoia, dizziness, confusion, increased heart rate, memory impairment, or combinations thereof. Generally speaking, such a method would comprise administering a pharmaceutically effective amount of THC and CBD, such that at least one biomarker of central and peripheral sensitization is modulated and migraine pain is reduced in the subject, while unwanted side effects or risk factors of THC are minimized.

In certain embodiments, the migraine pain is acute migraine pain. Generally speaking, a method of the invention is used for a subject suffering from an acute migraine. Methods of diagnosing acute migraine are known in the art. In some embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

(c) Reducing Migraine Frequency with a Minor Cannabinoid Composition

A minor cannabinoid composition of the present disclosure may be used in a method of reducing migraine frequency. Generally speaking, such a method would comprise administering a pharmaceutically effective amount of at least one minor cannabinoid alone, or in combination with THC, CBD, or both, such that at least one biomarker of central and peripheral sensitization is modulated and migraine frequence is reduced in the subject.

In some embodiments, the at least one minor cannabinoid, detailed in section I above, may be a phytocannabinoid. In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with chronic migraine or high frequency migraine. As used here, chronic migraine is defined as over 15 headache days per month. High frequency migraine is defined as 7-14 headache days per month. Methods of diagnosing chronic migraine or high frequency migraine are known in the art.

(d) Methods of Reducing Migraine Frequency with a THC and CBD Composition

A THC and CBD composition of the present disclosure may be used in a method of reducing migraine frequency. Generally speaking, such a method would comprise administering a pharmaceutically effective amount of THC and CBD, such that at least one biomarker of central and peripheral sensitization is modulated and migraine frequence is reduced in the subject, while unwanted side effects or risk factors of THC are minimized.

In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with chronic migraine or high frequency migraine. As used here, chronic migraine is defined as over 15 headache days per month. High frequency migraine is defined as 7-14 headache days per month. Methods of diagnosing chronic migraine or high frequency migraine are known in the art.

(e) Methods of Reducing Fibromyalgia Pain with a Minor Cannabinoid Composition

A minor cannabinoid composition of the present disclosure may be used in a method of reducing fibromyalgia pain. Generally speaking, such a method would comprise administering a pharmaceutically effective amount of at least one minor cannabinoid alone, or in combination with THC, CBD, or both, such that at least one biomarker of central and peripheral sensitization is modulated and fibromyalgia pain is reduced in the subject.

In some embodiments, the at least one minor cannabinoid, detailed in section I above, may be a phytocannabinoid. In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with fibromyalgia pain. Methods of diagnosing fibromyalgia pain are known in the art.

(f) Methods of Reducing Fibromyalgia Pain with THC and CBD Compositions

A THC and CBD composition of the present disclosure may be used in a method of reducing fibromyalgia pain. Generally speaking, such a method would comprise administering a pharmaceutically effective amount of THC and CBD, such that at least one biomarker of central and peripheral sensitization is modulated and fibromyalgia pain is reduced in the subject, while unwanted side effects or risk factors of THC are minimized.

In certain embodiments, the at least one biomarker is NMDA. In other embodiments, the at least one biomarker is glutamate. In still other embodiments, the at least one biomarker may include CGRP, FAAH, Substance P, 5-HT, NO, GABA, NGF, serotonin, dopamine, AEA, 2-AG, or others.

In particular embodiments, a subject may be diagnosed with fibromyalgia pain. Methods of diagnosing fibromyalgia pain are known in the art.

EXAMPLES

Example 1

Preclinical Model

The biomarkers and other indicators of activity of the present disclosure, which includes central and peripheral sensitization, may be observed using pre-clinical in vitro and in vivo models of migraine pain and frequency, fibromyalgia pain, and other pain models.

Migraine models used to observe the biomarker or activity may be in vitro and in vivo and may be vascular, neuronal, and behavioral models. In vitro vascular models may include models of vasodilation and vasoconstriction in isolated human or animal arteries and veins, or other models. Neurovascular models may include models targeting activation and modulation of the trigeminovascular system, for instance models of trigeminal stimulation and plasma protein extravasation, models of stimulation of the meninges, models of stimulation of the superior sagittal sinus, models of c-Fos expression within the trigeminal nucleus caudalis (TNC), models of nitric oxide donors, models of cortical spreading depression with a focus on 5HT-1B/1D receptors, CGRP receptors, or other receptors such as NMDA receptors, models of central pain sensitization focused on the trigeminal nerve, or other models.

In vivo vascular models may include models which measure arterial or veinal diameter of, for instance, the carotid arterial bed, arteriovenous anastomoses, and pial arteries, models of intravital microscopy, and models of meningeal blood flow, or other models. Anesthetized models may include models of intracranial dural stimulation, models of brainstem dysfunction/modulation, models of cortical spreading depression targeting aura, models of pharmacological provocation, or other models.

Behavioral models may include models of trigeminovascular nociception, models of spontaneous nociceptive responses in the craniofacial region, models of associated neurological symptoms, models of associated symptoms of migraine or sensitization such as photophobia, phonophobia, osmophobia, or other symptoms, or other models.

Genetic models may include CACNA1A mouse models, ATP1A2 mouse models, casein kinase 1 delta mouse models, TRESK mouse models, models targeting familial or sporadic hemiplegic migraine, or other models.

Models of chronic migraine may include models of nitroglycerin, models of medication overuse headache, models of spontaneous trigeminal allodynia, models of monogenic migraine mutation, or other models.

Models may be different vascular and neuronal models than the models described which incorporate techniques and tools such as laser doppler flowmetry, micro-iontophoresis and/or microinjection, histology and/or immunohistochemistry, biochemistry, evoked behavioral testing, spontaneous behavioral testing, conditioned placed preference or aversion, elevated plus or zero maze, or other models intended to measure the desired biomarker or indication of activity.

Other pain models which may be used may include peripheral inflammation and peripheral neurogenic inflammation models such as complete Freund's adjuvant (CFA), models applying carrageenan, mustard oil, bee venom, capsaicin, and formalin, models of chronic postischemia pain, models of chronic constriction injury, spinal nerve ligation, phototoxicity, distal nerve injury, complete nerve transection, trigeminal ganglion compression, experimental osteolytic sarcoma, experimental squamous cell carcinoma, experimental melanoma, models of muscle pain, or other models.

In each of the above models, it is expected that a composition of the present disclosure will reduce migraine pain or migraine frequency. Furthermore, other pain models detailed above may be used to demonstrate that a composition of the present disclosure reduces fibromyalgia pain.

Example 2

FHM Study

This study will evaluate cannabinoids combinations that normalize (1) cortical spreading depression (CSD) properties, (2) behavioral responses, and (3) parameters of neuroinflammation in FHM1 or FHM2 mice compared to WT mice.

The study will monitor altered cortical spreading depression (CSD) properties, via experiments inducing CSD. The study will also evaluate behavioral and neuroinflammatory responses in the context of allodynia. For instance, pain measurements, specifically von Frey filament testing of periorbital region or hind paw and pain-relevant behavior using a home-modified version of the mouse grimace scale (MGS) will be monitored. Assessment of pain-relevant behavior with MGS will be performed at 24, 48 and 72 hours after injection. Neuroinflammation will be assessed using immunohistochemistry (IHC) conducted on relevant brain sections using relevant markers e.g. of HMGB1, NF-κB, and microglial activation.

FHM1 transgenic mice will be compared to WT—for instance, comparing Thy1-ChR2 (Thy1-driven expression of Channel rhodopsin 2)/FHM1 to Thy1-ChR2/WT mice.

Different ratios and combinations of cannabinoids will be evaluated, including 100:1 and 30:1 ratio of CBD:THC mg/kg.

Example 3

Migraine Studies

Cannabinoid combinations will be evaluated using at least two migraine models. First, a peripheral injection of a nitric oxide (NO) donor nitroglycerin (NTG) aka glyceryl trinitrate (GTN) to induce migraine-like symptoms in mice—a generally accepted model extensively used and described and induces evoked and spontaneous pain in rodents. Second, a CGRP-induced migraine model will be evaluated.

Different ratios of CBD:THC will be tested to reduce NTG-induced migraine-like phenotypes in mice. Migraine-like behaviors in the mice (light aversion, periorbital tactile hypersensitivity, and facial signs of discomfort) will be evaluated. Animals will be injected with NTG or vehicle, and one of the following treatments: vehicle, CBD (1-100 mg/kg, i.p.), THC (1 mg/kg i.p. fixed dose), or a combination of CBD:THC (1:1, 3:1, 10:1, 30:1, 60:1, 100:1, and 300:1 where 300:1 is 300 mg/kg CBD and 1 mg/kg THC). Both male and female mice will be tested.

The adverse effects of the different combinations of CBD:THC will also be evaluated in mice. Experiments will test for depression (tail suspension), activity and motor alterations (voluntary wheel activity), and cognitive alterations (Y maze). Mice will be injected (i.p.) with vehicle, CBD, THC, or the different combinations of CBD:THC listed above. of central and peripheral sensitization; or (b) CBD, wherein the ratio of isolated minor cannabinoid(s) to CBD is selected to maximize the modulation of at least one biomarker of central and peripheral sensitization.

What is claimed is:

1. A method of reducing acute migraine pain, photophobia, phonophobia, nausea, or frequency in a subject, the method comprising administering a pharmaceutically effective amount of at least one minor cannabinoid in combination with THC and CBD such that at least one biomarker of central and peripheral sensitization is modulated and acute migraine pain, photophobia, phonophobia, nausea, or frequency is reduced in the subject, wherein the composition comprises 80 w/w % CBD to 99.9 w/w % CBD and 0.1 w/w % THC to 20 w/w % THC wherein the biomarker is selected from the group consisting of NMDA, glutamate, CGRP, FAAH, Substance P, NO, GABA, NGF, serotonin, dopamine, AEA, and 2-AG.

2. The method of claim 1, wherein the subject has chronic migraines.

3. The method of claim 1, wherein the subject suffers from high frequency migraine.

4. The method of claim 1, wherein the minor cannabinoid is selected from the group consisting of CBG, CBGA, CBN, CBNA, THCV, THCA, CBC, CBCA, CBDV, and D8-THC.

5. The method of claim 1, wherein the composition comprises 0.1 w/w % to 0.5 w/w % THC.

6. The method of claim 1, wherein the composition comprises 10 w/w % THC.

7. The method of claim 5, wherein the composition comprises 80 w/w % to 95 w/w % CBD.

8. A method of reducing acute migraine pain, photophobia, phonophobia, nausea, or frequency in a subject, the method comprising administering a pharmaceutically effective amount of at least one minor cannabinoid in combination with THC and CBD such that at least one biomarker of central and peripheral sensitization is modulated and acute migraine pain, photophobia, phonophobia, nausea, or frequency is reduced in the subject, wherein the composition comprises at least 90 w/w % CBD and no more than 10 w/w % THC wherein the biomarker is selected from the group consisting of NMDA, glutamate, CGRP, FAAH, Substance P, NO, GABA, NGF, serotonin, dopamine, AEA, and 2-AG.

* * * * *